US00PP13884P39

(12) United States Plant Patent
Fleming et al.

(10) Patent No.: US PP13,884 P3
(45) Date of Patent: Jun. 17, 2003

(54) DIANTHUS PLANT NAMED 'DOUBLE SPOTTY'

(76) Inventors: David W. Fleming, 8101 S. 14th St., Lincoln, NE (US) 68512; Gretchen A Zwetzig, 8101 S. 14th St., Lincoln, NE (US) 68512

( * ) Notice: Subject to any disclaimer, the term of this patent is extended or adjusted under 35 U.S.C. 154(b) by 10 days.

(21) Appl. No.: 09/798,389

(22) Filed: Mar. 5, 2001

(65) Prior Publication Data

US 2002/0124289 P1 Sep. 5, 2002

(51) Int. Cl.[7] ..... A01H 5/00

(52) U.S. Cl. ..... Plt./272

(58) Field of Search ..... Plt./272

*Primary Examiner*—Bruce R. Campell
*Assistant Examiner*—Annette H. Para

(57) ABSTRACT

A new and distinct cultivar of winter hardy Dianthus plant named 'Double Spotty' is the result of a unique hybridization. This new and distinct cultivar is characterized primarily as to novelty by its extreme cold hardiness to Zone 4, its cherry red flowers like Spotty but having multiple rows of petals. This everblooming cultivar has a nice compact form with vigorous growth.

2 Drawing Sheets

Botanical classification: *Dianthus hybrid.*
Variety denomination: 'Double Spotty'.

BACKGROUND OF THE NEW PLANT

The new plant of this invention is the result of a unique hybridization, with the breeding achievement being evidenced in the outstanding combination of characteristics exhibited by this new and distinct Dianthus plant, which include:

(a) Blue-green upright foliage that forms a neat and compact bun and compliments the gardenscape;

(b) Bright red flowers with double, pink, spot-like markings on each petal. The petals are arranged in approximately 3 to 4 rows, adding to the interest;

(c) The plant being very floriferous with flowers that bloom in the Spring, Summer and late Summer.

(d) The plant being medium-sized, but vigorous, with compact and uniform growth which gives it unique landscape utility; and (e) The plant being so hardy that it can consistently withstand winter temperatures of at least −30 degrees Fahrenheit.

SUMMARY OF THE INVENTION

Double Spotty was the result of a 40-year breeding program. Its ancestry includes *D. grantianapolitanus, D. plumarius*, and *D neglectus*. More specifically, the plant resulted from a selected seedling of Spotty (a Fleming introduction). The seedling which most nearly met all above named standards was selected.

This new plant first bloomed in the summer of 1985 and was selected by David Fleming and Gretchen Zwetzig on David Fleming's property in Lincoln, Nebr. Asexual propagation of the plant by cuttings and root division in Lincoln, Nebr., has shown that the unique and distinguishing features of the plant are faithfully transmitted from generation to generation and appear to be fixed.

Since its origin, the plant has bloomed from midsummer until frost, while exhibiting the above-mentioned distinctive characteristics. This hardy Dianthus plant contributes to the market with its sheer beauty, its compact growth habit, its great resistance to disease and insects, its stability through extremes in rain and drought, and its extreme hardiness.

BRIEF DESCRIPTION OF THE DRAWINGS

The flower, bud, foliage, and growth habit of the plant are shown in the attached illustrations. More specifically, Sheet 1 shows a close-up of the flower and Sheet 2 shows the habit of the hybrid. The flower/plant colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE and number designations are in accordance with the *Dictionary of Color* (Maerz and Paul), while general color recitations are consistent with ordinary American color terminology.

'Double Spotty' has not been observed under all possible environmental conditions. It is to be understood that the phenotype may vary significantly with variations in the environment such as temperature, light intensity, and day length, without, however any difference in genotype of the plant. The following botanical characteristics and observations are taken from the plant when grown under normal outdoor conditions in Lincoln, Nebr.

THE PLANT

Parentage:

*Seed parent.*—Spotty *D. plumarius, D. neglectus*, and *grantianapolitanus.*

*Pollen parent.*—'Horatio', *D. neglectus.*

How new variety differs from parents and similar cultivars: The new variety of Dianthus differs in its more compact stature, its larger, multilayered red flowers, with pink spots on each petal, its strong spicier odor and its improved vigor and hardiness.

Origin: A selected seedling from the above-stated cross.

Type of plant: Hardy herbaceous perennial.

Propagation: Relatively easy to propagate; holds its distinguishing characteristics through successive propagations by cuttings.

Age of plant described: Approximately 3 years of age; grown under normal NE temperatures (Zone 4).

Size: About 7–12" tall and 12" wide.

Form: Symmetrical annual growth from perennial roots.

Habit: Upright with many uniform branches. Forms a compact "bun".

Growth: Vigorous; medium and compact.

Hardiness: Hardy to at least −30 degrees Fahrenheit.

General health: Plant is very resistant to diseases , such as: fungus and viruses, etc.; very resistant to pests such as: spider mites, scale, mealy bugs, aphids, etc.

Foliage:

1. *Quantity.*—Abundant.
2. *Linear-lanceolate.*—Slightly reflexeing to apx. 45% from the stem, but not curled under.
3. *Size.*—5 cm in length; 3 mm in width.
4. *Color.*—Silvery blue-green I-5, PLATE 30, page 83 of the Dictionary of Color.
5. *Surface texture.*—Glabrous.
6. *Ribs and veins.*—Ribs slightly depressed; veins not visible to the eye.
7. *Rachis.*—Slightly raised on underside of leaf.
8. *Internode length.*—½ to 1½ inches or 1.5 to 4 cm.
9. *Main stem length.*—12" or 24 cm.

THE BUD

Size: Small.

*Diameter.*—½ cm.

*Length.*—1½–2 cm.

Form: Ovoid.

Opening rate: Normal.

Color of petals: When bud is opening: 2-F, PLATE 2,page 27.

Sepals:

*Shape.*—Jointed at the base with acute character and sharp apexes. The sepals are sturdy to half-way up the bud.

*Margins.*—Smooth.

*Base.*—United, straight.

Calyx:

*Size.*—Small.

*Shape.*—Bell-shaped.

*Splitting.*—At the base. Overlapping sepals.

*Aspect.*—Smooth.

Flower stem:

*Length.*—To about 15 cm.

*Character.*—Erect.

*Color.*—a-7, PLATE 29, page 81.

THE FLOWER

Blooming period: "Everblooming". Profuse from mid-May until early September.

Average flower diameter: Medium; about 1½" or 4 cm.

Borne: Singly

Petal shape:

*Apex.*—Rounded.

*Base.*—Lengthened.

*Margin.*—Crenate.

Overall shape of flower: Almost dome-shape with several rows of petals (3–5).

Petalage: Number of petals is 15–20.

Arrangement: Alternate and overlapping in layers.

Surface texture: Soft with satin appearance.

Form: Fan-shaped and rounded.

Coloration:

*Petals.*—6-K, PLATE 5, page 33.

*Markings.*—2-F, PLATE 2, page 27.

*Reverse of petals.*—2F, PLATE 2, page 27.

Fragrance: Sweet and spicy clove.

Reproductive organs:

1. *Stamens.*—Number 3–11. Arrangement: Around the pistils. Anthers: Size: 4 mm. Color: whitish. Filaments: Length: less than 4 mm. Color: whitish.
2. *Pistils.*—Number: Two. Styles: Color: white Stigmas: Color: white.
3. *Character of ovaries.*—Cone-shaped.

THE FRUIT

Seed size: 3 mm.

Shape: Globular or kidney-shaped.

Texture: Smooth.

Color: Black.

GENERAL OBSERVATIONS

This plant, as a hybridized hardy everblooming Dianthus, is valuable to the landscape market for its improvements in the addition of rows of petals on the charming Spotty Dianthus, its all-around vigor, dense and compact breaking action, and adaptation to extreme environments, including the ability to consistently survive winter temperatures of at least −30 degrees Fahrenheit.

We claim:

1. A new and distinct cultivar of Dianthus plant, as herein shown and described, characterized by its neat and compact blue-green foliage, its enhanced Spotty-like flowers of cherry red with soft pink spots and its "everblooming" vigor, and its hardiness.

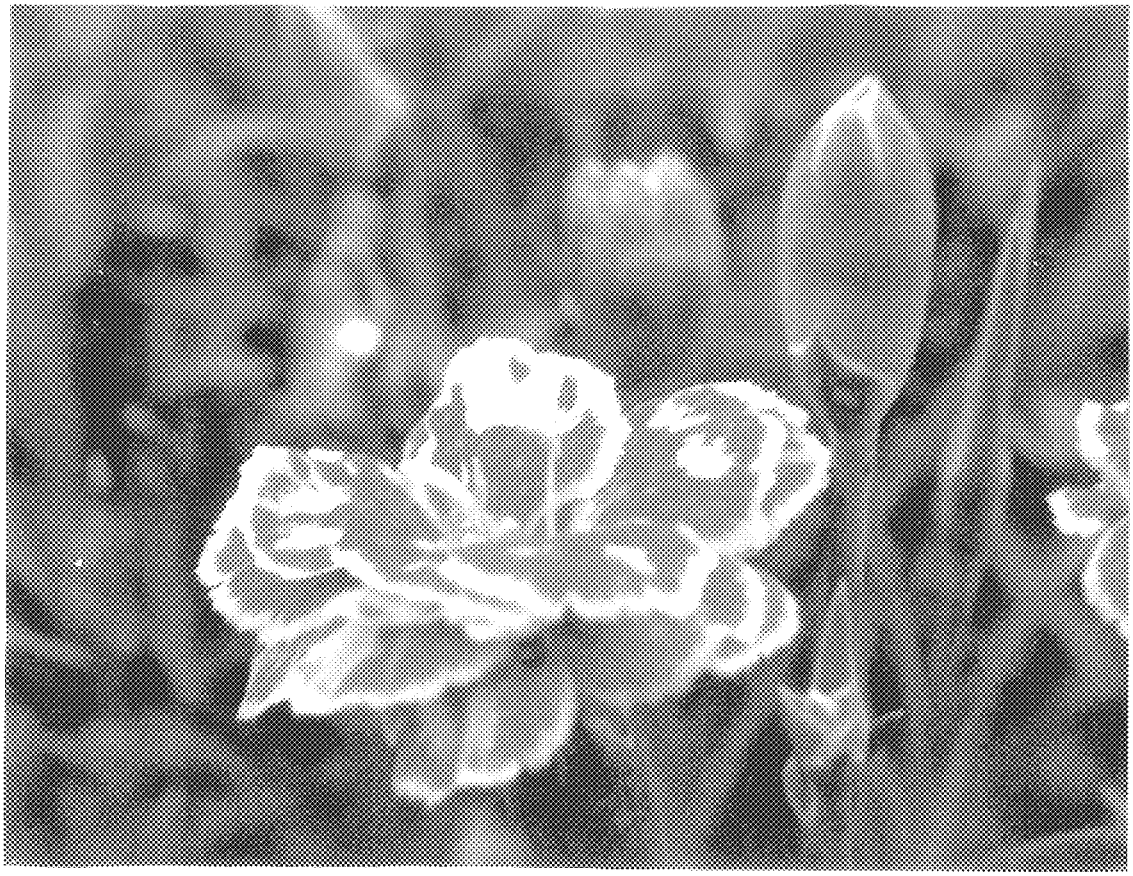

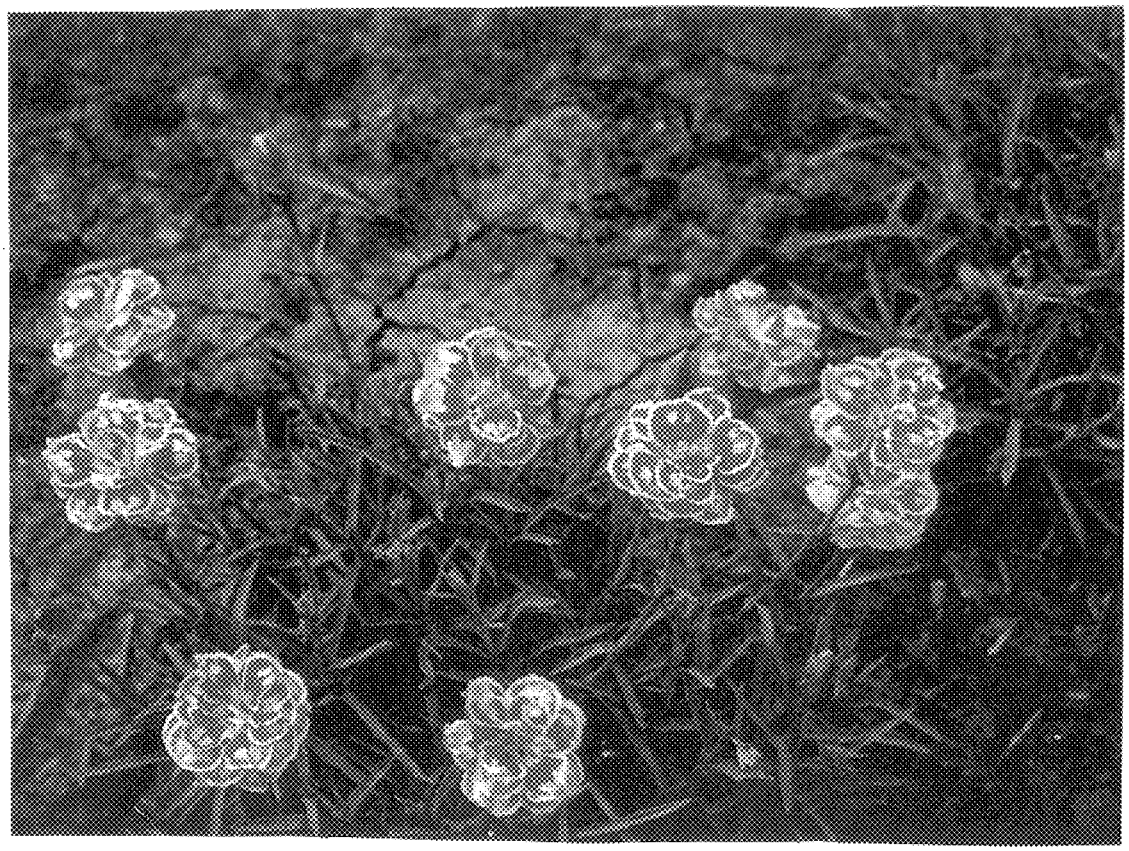

* * * * *